(12) United States Patent
Mohammadi et al.

(10) Patent No.: US 8,491,926 B2
(45) Date of Patent: *Jul. 23, 2013

(54) METHOD AND SYSTEM FOR AUTOMATIC OR MANUAL EVALUATION TO PROVIDE TARGETED AND INDIVIDUALIZED DELIVERY OF COSMETIC ACTIVES IN A MASK OR PATCH FORM

(75) Inventors: Fatemeh Mohammadi, Hauppauge, NY (US); Tsung-wei Robert Mou, Stony Brook, NY (US); Lisa Ou, Flushing, NY (US)

(73) Assignee: ELC Management LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/962,807

(22) Filed: Dec. 8, 2010

(65) Prior Publication Data

US 2011/0300196 A1    Dec. 8, 2011

Related U.S. Application Data

(63) Continuation-in-part of application No. 12/781,897, filed on May 18, 2010, now Pat. No. 8,358,348, which is a continuation-in-part of application No. 12/533,107, filed on Jul. 31, 2009, now Pat. No. 8,425,477.

(60) Provisional application No. 61/097,273, filed on Sep. 16, 2008.

(51) Int. Cl.
*A61K 9/70* (2006.01)
*H04N 5/225* (2006.01)

(52) U.S. Cl.
USPC ........... 424/443; 424/402; 348/207.1; 347/86

(58) Field of Classification Search
USPC .................. 424/443, 402; 348/207.1; 347/86
See application file for complete search history.

(56) References Cited

U.S. PATENT DOCUMENTS

| | | |
|---|---|---|
| 3,154,070 A | 10/1964 | Meckelburg |
| 3,499,446 A | 3/1970 | Tsuneizumi et al. |
| 5,016,173 A | 5/1991 | Kenet et al. |
| 5,538,732 A | 7/1996 | Smith et al. |
| 5,622,692 A | 4/1997 | Rigg et al. |
| 5,958,560 A | 9/1999 | Ewan |
| 6,001,380 A | 12/1999 | Smith et al. |
| 6,293,284 B1 | 9/2001 | Rigg |
| 6,502,583 B1 | 1/2003 | Utsugi |
| 6,516,245 B1 | 2/2003 | Dirksing et al. |
| 6,530,379 B2 | 3/2003 | Iosilevich |
| 6,571,003 B1 | 5/2003 | Hillebrand et al. |
| 6,574,801 B1 | 6/2003 | Harens et al. |
| RE38,246 E | 9/2003 | Leonard et al. |
| 6,761,697 B2 | 7/2004 | Rubinstenn et al. |
| 6,770,286 B1 | 8/2004 | Berry |
| 6,810,130 B1 | 10/2004 | Aubert et al. |
| 6,856,861 B2 | 2/2005 | Dirksing et al. |
| 6,937,755 B2 | 8/2005 | Orpaz et al. |
| 6,959,119 B2 | 10/2005 | Hawkins et al. |
| 7,006,657 B2 | 2/2006 | Bazin |
| 7,079,158 B2 | 7/2006 | Lambertsen |
| 7,165,559 B1 | 1/2007 | Goodman |
| 7,324,668 B2 | 1/2008 | Rubinstenn et al. |
| 7,387,787 B2 | 6/2008 | Fox |
| 7,424,139 B1 | 9/2008 | Stefan et al. |
| 7,437,344 B2 | 10/2008 | Peyrelevade |
| 7,634,103 B2 | 12/2009 | Rubinstenn et al. |
| 8,077,931 B1 | 12/2011 | Chatman et al. |
| 2002/0090123 A1 | 7/2002 | Bazin |
| 2003/0063794 A1 | 4/2003 | Rubinstenn et al. |
| 2004/0022830 A1 | 2/2004 | Nakamura et al. |
| 2004/0078278 A1 | 4/2004 | Dauga et al. |
| 2004/0102750 A1 | 5/2004 | Jameson |
| 2006/0104931 A1 | 5/2006 | Fukutome et al. |
| 2006/0197775 A1 | 9/2006 | Neal |
| 2007/0258656 A1 | 11/2007 | Aarabi |
| 2008/0014231 A1 | 1/2008 | Okano |
| 2008/0058915 A1 | 3/2008 | Chang |
| 2008/0163344 A1 | 7/2008 | Yang |
| 2009/0129631 A1 | 5/2009 | Faure et al. |
| 2009/0133206 A1 | 5/2009 | Benjamin et al. |
| 2009/0231356 A1 | 9/2009 | Barnes et al. |
| 2009/0260648 A1 | 10/2009 | Castelluccio |
| 2010/0226531 A1 | 9/2010 | Goto |

FOREIGN PATENT DOCUMENTS

| | | |
|---|---|---|
| DE | 102005020938 A1 | 11/2006 |
| EP | 1433418 A1 | 6/2004 |
| EP | 1 459 782 | 9/2004 |
| EP | 1813167 | 8/2007 |
| JP | 55-164623 A | 12/1980 |

(Continued)

OTHER PUBLICATIONS

Supplementary European Search Report; EP09814947; Completion Date: Oct. 10, 2011; Date of Mailing: Oct. 24, 2011.
PCT International Search Report; International Application No. PCT/US2009/052525; Completion Date: Feb. 25, 2010; Date of Mailing: Mar. 2, 2010. (Related U.S. Appl. No. 12/533,107).

(Continued)

*Primary Examiner* — Gina C Justice
(74) *Attorney, Agent, or Firm* — Martin W. Haerter (57) ABSTRACT

A system and method are provided for targeted and individualized delivery of multiple skin benefit agents to the skin of a user. The image of a predetermined treatment area of the user's skin is first captured by an imaging device. Selective data input from analysis tools and the end user is then analyzed by a computing device to generate a unique skin profile for the user, which is indicative of the skin conditions at the predetermined treatment area. Based on such skin profile, a printing device prints out one or more cosmetic delivery sheets that can be applied to the predetermined treatment area. Each of the cosmetic delivery sheets contains a substrate with multiple isolate, discrete regions, while at least two of the regions are imprinted with different skin benefit agents for treating different skin conditions of the predetermined treatment area according to the unique skin profile of the user.

2 Claims, 9 Drawing Sheets

FOREIGN PATENT DOCUMENTS

| | | |
|---|---|---|
| JP | 7-231883 | 9/1995 |
| JP | 08-308634 | 11/1996 |
| JP | 2001-346627 | 12/2001 |
| KR | 20-0416534 | 5/2006 |
| KR | 10-2008-0059157 | 6/2008 |
| TW | 200426655 | 12/2004 |
| WO | WO97/29441 | 8/1997 |
| WO | WO98/37811 | 9/1998 |
| WO | WO00/00059 | 1/2000 |
| WO | WO01/04840 | 1/2001 |
| WO | WO 02/01499 | 1/2002 |
| WO | WO2005/058114 | 6/2005 |
| WO | WO2007/006559 | 1/2007 |
| WO | WO2007/021972 | 2/2007 |
| WO | WO2007/123380 | 11/2007 |
| WO | WO 2008/010167 | 1/2008 |
| WO | WO2009/137277 | 11/2009 |

OTHER PUBLICATIONS

PCT Written Opinion of the International Searching Authority, or the Declaration; International Application No. PCT/US2009/052525; Completion Date: Feb. 25, 2010; Mailing Date: Mar. 2, 2010. (Related U.S. Appl. No. 12/533,107).

PCT International Search Report; International Application No. PCT/US2009/041618; Completion Date: Dec. 4, 2009; Date of Mailing: Dec. 4, 2009. (Related U.S. Appl. No. 12/410,118).

PCT Written Opinion of the International Searching Authority, or the Declaration; International Application No. PCT/US2009/041618; Completion Date: Dec. 4, 2009; Mailing Date: Dec. 4, 2009. (Related U.S. Appl. No. 12/410,118).

PCT International Search Report; International Application No. PCT/US2011/036288; Completion Date: Jan. 31, 2012; Date of Mailing: Feb. 9, 2012.

PCT Written Opinion of the International Searching Authority; International Application No. PCT/US2011/036288; Completion Date: Jan. 31, 2012; Mailing Date: Feb. 9, 2012.

PCT International Search Report; International Application No. PCT/US2011/036292; Completion Date: Jan. 31, 2012; Date of Mailing: Feb. 9, 2012.

PCT Written Opinion of the International Searching Authority; International Application No. PCT/US2011/036292; Completion Date: Jan. 31, 2012; Mailing Date: Feb. 9, 2012.

METHOD AND SYSTEM FOR AUTOMATIC OR MANUAL EVALUATION TO PROVIDE TARGETED AND INDIVIDUALIZED DELIVERY OF COSMETIC ACTIVES IN A MASK OR PATCH FORM

CROSS-REFERENCE TO RELATED APPLICATIONS

This application claims all the priority of, and is a CIP of U.S. Non-Provisional patent application Ser. No. 12/781,897 filed May 18, 2010. The '897 application claims priority from, and is a CIP of U.S. Non-Provisional patent application Ser. Nos. 12/533,107 filed Jul. 31, 2009, which claims priority from U.S. provisional application 61/097,273 filed Sep. 16, 2008. The '897 application also claims priority from U.S. Ser. No. 12/410,118 filed Mar. 24, 2009, which claims priority from U.S. 61/097,273 filed Sep. 16, 2008 and U.S. 61/051,774, filed May 9, 2008.

FIELD OF THE INVENTION

The present invention relates to method and system for achieving targeted and individualized delivery of one or more skin benefit agents to the skin of an user in need of such skin benefit agents, and to devices in the form of a single-use sheet for containing and delivering the skin benefit agents to one or more targeted areas of the skin. In particular, the invention relates to a method of delivering one or more skin benefit agents to targeted areas of the facial skin of a user based on the unique skin profile of such user and to a cosmetic sheet mask which incorporates one or more cosmetic or dermatological preparations for application to and treatment of the targeted areas of the skin of the user.

BACKGROUND OF THE INVENTION

A variety of cosmetic patches or devices are commercially marketed or described as being useful for the delivery of skin care actives such as vitamins, anti-acne actives, moisturizers, and the like. It has been known to use cosmetic sheets comprised of various materials, such as non-woven cotton, elastically extendable or stretchable materials, thermoplastics, tacky gel, etc., impregnated with various cosmetic or dermatological preparations, for application to the skin of the face, the neck and other areas of the body. The cosmetic sheets comprise a flexible support adapted to conform to the target areas when applied. The sheets also contain a system for containing and delivering skin benefit agents to the skin to which the sheet is applied. Currently, however, facial sheet masks on the market are fully impregnated with active ingredients and are applied to the entire face so as to deliver these ingredients to the entire face. Alternatively, a patch is applied only to certain areas, such as, under the eyes, to deliver the skin benefit agent to only this locus. However, these articles suffer drawbacks resulting in undesirable in-use characteristics as perceived by the consumer. For example it has heretofore not been possible with known full facial masks to target one or more specific areas with one or more skin benefit agents, but only to treat the entire face with one composition. Most consumers have different concerns for their skin in different areas of their face. For example many consumers have combination skin in which the T-zone area (forehead, nose and chin) is oily while the remainder of the face is dry. For another example some consumers may have lines and wrinkles at the forehead, eye, and mouth areas, dry or flaky skin at the cheek areas, and hyper-pigmentation spots at other areas. Each region would need different treatment products to address the different concerns. Conventional masks can only address one concern at a time by treating the entire facial skin, rather than only the targeted areas.

There is therefore a need by consumers for cosmetic sheets which can deliver multiple skin benefit agents to various targeted areas of the skin of a user to address different skin conditions of such a user based on his or her unique skin profile.

SUMMARY OF THE INVENTION

The cosmetic sheets according to the present invention are provided with discrete regions, which are imprinted with different skin benefit agents, so when such cosmetic sheets are applied to and conformed to the skin, they can accurately deliver pre-determined dosages of different skin care formulations to the skin for treating different skin conditions or providing different skin benefits. More preferably, the cosmetic sheets of the present invention are not mass-produced like the conventional "one-type-fits-all" products, but are specifically customized for individual users according to their unique skin profiles.

Accordingly, the present invention in one aspect relates to a system for targeted and individualized delivery of multiple skin benefit agents to the skin of a user. Such system includes at least: (a) an imaging device for capturing an image of a desired treatment area of the user's skin; (b) means for generating a skin profile indicative of the actual or perceived conditions of the predetermined treatment area of the user's skin; and (c) a printing device communicatively connected with the analyzing device for printing one or more cosmetic delivery sheets, wherein the cosmetic delivery sheets are arranged and constructed for conforming to the predetermined treatment area of the user's skin, wherein each of the cosmetic delivery sheets comprises a substrate with multiple isolate, discrete regions, wherein at least two of the isolate, discrete regions are imprinted with different skin benefit agents for treating different skin conditions of the predetermined treatment area according to the skin profile generated by the generating means.

The present invention in another aspect relates to a cosmetic delivery sheet arranged and constructed for conforming to a predetermined treatment area of the skin of a user. Such a cosmetic delivery sheet includes at least a substrate with multiple isolate, discrete regions, wherein at least two of the isolate, discrete regions are imprinted with different skin benefit agents for treating different skin conditions of the predetermined treatment area.

The present invention in a further aspect relates to a printer that contains cartridges filled with compositions containing skin benefit agents. Preferably, but not necessarily, such a printer is constructed to print the skin benefit agents onto a substrate through a heatless printing process.

The present invention in yet another aspect relates to a method for targeted and individualized delivery of multiple skin benefit agents to the skin of a user, which includes at least: (a) capturing an image of a predetermined treatment area of the user's skin; (b) manually or automatically analyzing the captured image data as well as additional data captured via skin analysis tools and responses of the user to questionnaires; (c) manually or automatically generating a skin profile indicative of the conditions of the predetermined treatment area of the user's skin; and (d) printing one or more cosmetic delivery sheets based on the generated skin profile, wherein the cosmetic delivery sheets are arranged and constructed for conforming to the predetermined treatment area of the user's skin, wherein each of the cosmetic delivery sheets comprises a substrate with multiple isolate, discrete regions, wherein at least two of the isolate, discrete regions are imprinted with different skin benefit agents for treating different skin conditions of the predetermined treatment area.

Other aspects and objectives of the present invention will become more apparent from the ensuing description, examples, and claims.

DETAILED DESCRIPTION OF THE INVENTION AND PREFERRED EMBODIMENTS THEREOF

Reference will now be made in detail to exemplary embodiments of the invention. It is contemplated that a computerized or computer-aided system is used for achieving the targeted and individualized delivery of multiple skin benefit agents to the skin of a user based on the unique skin profile of the user created by manual or automatic analysis. Cosmetic delivery products produced by the system of the present invention are capable of delivering multiple skin benefit agents to multiple target sections or regions on demand and according to the user skin profile with precise dosage and location control.

Preferably, such a system includes at least an imaging device for capturing an image of the desired treatment area of the user's skin. Such desired treatment skin area may be, for example, full face, partial face, neck, thigh, or the like. In a particularly preferred but not necessary embodiment of the present invention, the desired treatment area is the full face of the user. The imaging device is preferably a digital camera, which may capture the images of the desired treatment area in conjunction with a light source that delivers sufficient and consistent visible or invisible light, such as white light, infrared light or near infrared light. The imaging device can be set in either a manual or an automatic mode for identifying the desired treatment area.

The captured images are converted into digital data and stored on a suitable medium, for example, in the imaging device and/or in a computer and/or in a dedicated storage device that is permanently or selectively communicatively connected with the imaging device and/or computer. The captured images may be transmitted between devices as, for example, digital data, via a direct connection between the imaging device and the computer or storage device, or via a network, e.g., LAN, WAN, telephonic or internet network (in any form of transmission medium, e.g., coaxial cable, fiber optic cable, CAT 5 cable, cell phone, satellite or other radio, optic or electronic transmission, etc., or manually by, for example, transferring the captured images to a memory medium (e.g., a memory card, portable disk drive, flash drive, etc.) and transporting the memory medium from one device to another.

The system may include means for generating a skin profile indicative of the various conditions in need of treatment. Preferably, the skin profile defines skin regions with certain defects that need certain types of treatment. The term "defects" as used herein broadly covers any types of suboptimal skin conditions, such as skin dryness, flakiness, redness, oiliness, large pores, dullness, dark spots, uneven skin tone, acne scars, fine lines and wrinkles, under-eye dark circles, under-eye puffiness, cellulite, and the like, or any types of abnormal skin conditions or disorders. More preferably, the skin profile also defines the severity of the skin defects.

In a preferred embodiment, the means for generating a skin profile includes computer software associated with a computing device such as a personal computer, a central computer, or a computer server that is part of a larger computer bank or network. The computer software and associated computing device is programmed to receive data about an individual user, process the data and generate a customized skin profile for that user showing various skin conditions and corresponding locations of the skin conditions in the captured images. The same computer software and associated computing device and/or another software and computing device may also be programmed to generate recommendations for treatment of the various skin conditions identified in the skin profile.

The means for generating a skin profile may receive data in the form of inputs from automated data imaging or collection devices, such as, the aforementioned digital imaging device or other commercially available, stand-alone or hand-held skin imaging or analysis tools that can be used for diagnosing skin conditions including, for example, skin pH meters, moisture meters, elasticity meters, scope cameras, etc. Non-limiting examples of diagnostic tools include the VISIA® Complexion Analysis tools available from Canfield Scientific, Inc. (Fairfield, N.J.), spectral camera systems, thermal camera systems, laser Doppler imaging systems, translucency meters, moisture meters, mexameters, Mexameter® MX18 available from CK Electronic (Koln, Germany), the CR series Chroma Meters available from Konica Minolta Business Solutions, U.S.A. (Ramsey, N.J.), the SIAMETRICS™ and COSMETRICS™ skin visualization and measurement systems available from Astron Clinica Ltd. (Cambridge, United Kingdoms), and the like.

Alternatively, or in combination with the data received from the foregoing automated imaging or analysis devices, the means for generating a skin profile may receive data in the form of selective inputs from an input device such as, for example, a keyboard or touch screen associated with home computer, personal digital assistant (PDA), a cell phone or smart phone, a point-of-sale terminal, a kiosk, a workstation or the like. A beauty operator would selectively enter the inputs. The beauty operator may be, for example, a skin specialist, a beauty advisor, a cosmetician, a dermatologist or a sales associate associated with product sales or recommendation in, for example, a beauty counter environment in a brick-and-mortar type retail store. Alternatively, the beauty operator may be remotely located and accessed by a user (i.e., a consumer, a purchaser or a product end user) via electronic means, such as, for example, emails, text messaging, instant messaging, chat sessions or social networking websites. In each case, the beauty operator would elicit at least some data from the end user, and conduct a visual analysis of the end user's actual appearance or an image or images submitted by the end user. This information would be supplemented with data based on diagnosis and recommendation protocols created in advance by the product retailer or product manufacturer. Alternatively, the beauty operator may elicit data from the user via a questionnaire designed for such purpose. The operator would diagnose skin conditions and make product recommendations, each of which can be mapped to a particular site or region of the treatment area of the user's skin. The mapping may occur via a mouse guided screen pointer or a touch screen input device directly on the image of the desired treatment area captured by the imaging device.

Alternatively, or in combination with the beauty operator, the user (consumer or end user) may input data directly through an input device such as a home computer, keyboard, touch screen, kiosk, cell phone or PDA. This may occur under the guidance of a beauty operator, or it may occur independently. The user would upload an image taken for example, with a digital camera, a cell phone, a PDA or a camera mounted on the home computer or kiosk.

With respect to the questionnaire used to elicit data from the user either with the assistance of the beauty advisor or independently, the questionnaire is designed to elicit both objective and subjective information. For example, the questionnaire may ask if the user's skin is oily, a relatively objective question. Alternatively, the questionnaire may ask the user to what degree they believe their skin is oily, a relatively subjective question. The questionnaire may also ask the consumer what problems they perceive themselves to have and what problems they are most concerned with solving—also relatively subjective questions. The objective and subjective answers to the questions may be input as data into the system where the computer software and associated computing device is programmed to process the data and generate a customized skin profile for that individual user showing various skin conditions and corresponding locations of the skin conditions in the captured image(s). The system is also programmed to generate recommendations for treatment of the various skin conditions identified in the skin profile, including the perceived and/or actual problem conditions.

As described in co-pending U.S. patent application Ser. No. 12/533,107 and above, inputs for the means for generating a skin profile may be generated by an analyzing device that is programmed for analyzing image data and generating a skin profile indicative of the conditions of the desired treatment area of the user's skin based on the image data. Such skin profile can be generated using various known algorithms. Examples of these algorithms are described in greater detail by Japanese Patent Application Publication No. 95-231883 entitled "Skin Surface Analysis System and Skin Surface Analysis Method"; International Patent Application Publication No. WO98/37811 entitled "Systems and Methods for the Multispectral Imaging and Characterization of Skin Tissue"; and U.S. Pat. No. 5,016,173 entitled "Apparatus and Method for Monitoring Visually Accessible Surfaces of the Body," the contents of which are incorporated in their entireties for all purposes. Commercially available skin imaging tools that can be used for diagnosing skin defects in the present invention include, for example, the VISIA® Complexion Analysis tools available from Canfield Scientific, Inc. (Fairfield, N.J.), thermal camera system, laser Doppler imaging system, translucency meter, mexameter, Mexameter® MX18 available from CK Electronic (Koln, Germany), the CR series Chroma Meters available from Konica Minolta Business Solutions, U.S.A. (Ramsey, N.J.), the SIAMETRICS™ and COSMETRICS™ skin visualization and measurement systems available from Astron Clinica Ltd. (Cambridge, United Kingdoms), and the like. Additionally, the captured image and other data can be processed through a 3D face modeling program such as, for example, FaceGen (www.facegen.com) for mapping the individual's facial features, skin defects and treatment areas in 3D. The 3D mapped face will further allow more precise location of treatment areas to create a 'tailor made' skincare product to fit an individual's exact facial features and dimensions. The 3D mapping will also allow display of a 3D 'virtual' head of the user that may be manipulated and used as a 'drawing board' to facilitate creation and further refinement of the tailor made, individualized skincare product. This 3-D face modeling feature creates a "virtual mirror" environment for the user. The operator or user can freely rotate and zoom the "virtual mirror" image (i.e., the virtual face or head image) on the display or monitor during subsequent skin profile evaluation steps and during personalized product creation steps. The virtual mirror environment creates a self mirror image of the face, which in turn facilitates and simplifies the evaluation and personalized product creation steps. This enhances the high-touch shopping experience for the user.

The skin profile including suggested actives and treatment areas can be adjusted by the user based on objective or subjective desires. The user driven selection process may also include color choices or aesthetic patterns that may be provided to the final mask to enhance the usability (i.e., locating treatment areas), desirability (i.e., aesthetic appeal), engagement and interactivity (i.e., playfulness of the user) of the product. If the severity of the skin defects is represented by a numerical value, it may be desirable to normalize such value based on the user's ethnic origin, age, geographic location, or any other factor that may have an impact on the user's skin conditions.

Once the skin profile is generated and saved, it may be processed by any suitable photo-editing and illustration software programs, such as Adobe Photoshop Element 4.0, Microsoft PowerPoint 2003, and the like, for creating images to be outputted to a printing device, which correspondingly print out one or more cosmetic delivery sheets that are customized for the user based on his or her unique skin conditions. Alternatively, a custom software program may be written for processing and printing cosmetic delivery sheets. Preferably, the printing device is a printer that contains multiple cartridges, each of which is filled with a composition containing one or more skin benefit agents. Because the conventional thermal inkjet printing mechanism may produce a high temperature environment at the print head during ink discharging step, which may degrade or destabilize certain skin benefit agents, it is preferred that the printing in the present invention is carried out using a heatless printing mechanism. For example, a pressure-driven ink jet can be used, in which pressure is created on demand by a piezoelectric transducer to change the shape of an internal diaphragm in the inkjet print head and therefore force droplets of the skin benefit agents contained in the ink tank to be deposited onto the substrate. Suitable printing devices for the practice of the present invention include, for example, the Epson Workforce series, preferably Epson Workforce 30, the Spectra piezoelectric printers from Fujifilm Dimatix, the RISO HC5500 inkjet printer, and the like. Alternatively, when the skin benefit agents to be delivered are thermally stable or relatively less susceptible to thermal degradation, conventional thermal ink-jet printers or low-heat inkjet printers can be used for practice of the present invention.

By using the above-described heatless printing process, the present invention successfully achieves delivery of multiple skin benefit agents with little or no reduction in their biological activities. First, the heatless printing process causes little or no degradation of the skin benefit agents. Second, certain skin benefit agents that are known to interfere with each other's biological activities can be placed into separate cartridges and deposited onto the substrate as separate droplets. More importantly, the droplets of such interfering skin benefit agents are sufficiently small in size that they can be arranged in a scattered manner. Consequently, such skin benefit agents can provide simultaneous treatments to the same region, but without having to be mixed with each other.

The cosmetic delivery sheets so printed could be used anywhere on the face or body skin to predetermined areas for delivery of ingredients via a sheet material mask or patch or similar system. The exact size and shape of the cosmetic sheet will depend upon the intended use and product characteristics. The cosmetic sheets will have sufficient flexibility, and a size and shape adapted to conform to the desired treatment area of the user's skin. In a particularly preferred, but not necessary, embodiment of the present invention, the cosmetic sheet is a facial mask adapted to conform to facial features. It will be understood that a variety of shapes and sizes may be accommodated according to the invention. Such a cosmetic sheet may include a flexible substrate that is formed of, preferably but not necessarily, water-soluble or non-water soluble materials, such as sugar or polysaccharides, collagen, and water-soluble film-forming polymers. The substrate contains multiple isolate, discrete regions, while at least two of such regions are imprinted with different skin benefit agents for treating different skin conditions according to the skin profile of the user.

Suitable skin benefit agents can be used in the present invention include, but are not limited to: anti-wrinkle or skin-tightening agents; anti-aging agents; moisturizing agents; skin-whitening or depigmentation agents; anti-inflammatory agents; anti-acne agents; DNA repair agents; skin lipid barrier repair agents; anti-cellulite agents; wound-healing agents; stretch-mark/scar removing agents; plumping agents; hair growth retardation agents; hair growth stimulating agents; dark cycle reduction or de-puffing agents; collagen synthesis or blood circulation enhancing agents; antioxidants; sebum-controlling agents; and pore-minimizing agents. Exemplary anti-wrinkle agents include, but are not limited to, acetyl hexapeptide-8, palmitoyl oligopeptide, dipeptide diaminobutyroyl, benzylamide diacetate, and the like. Exemplary skin-tightening agents include, but are not limited to, algae extract, pullulan, sweet almond seed extract, carbomer, palmitoyl oligopeptide, palmitoyl tetrapeptide-7, *Quercus suber* extract, and the like. Exemplary anti-aging agents include, but are not limited to, teprenone, trisodium resveratrol triphosphate, *Polygonum cuspidatum* root extract, whey protein, and the like. Exemplary moisturizing agents include, but are not limited to, hyaluronic acid, glycerin, urea, trehalose, and the like. Exemplary skin-whitening or depigmentation agents include, but are not limited to, ascorbic acid, magnesium ascorbyl phosphate, aminopropyl ascorbyl phosphate, mulberry root extract, *Scutellaria baicalensis* extract, grape extract, ferulic acid, hinokitol, and the like. Exemplary anti-inflammatory agents include, but are not limited to, spike moss extract, seal whip extract, *Polygonum cuspidatum* root extract, and the like. Exemplary anti-acne agents include, but are not limited to, salicylic acid, glycolic acid, lactobionic acid, and the like. Exemplary DNA repair agents include, but are not limited to, C1-C8 alkyl tetrahydroxycyclohexanoate, *micrococcus* lysate, bifida ferment lysate, and the like. Exemplary skin lipid barrier repair agents include, but are not limited to, phytosphingosine, linoleic acid, cholesterol, and the like. Exemplary anti-cellulite agents include, but are not limited to, *Coleus forskohlii* root extract, *Magnolia grandiflora* bark extract, *Nelubo nucifera* leaf extract, and the like. Exemplary wound-healing agents include, but are not limited to, *Mimosa tenuiflora* bark extract, soybean protein, and the like. Exemplary plumping agents include, but are not limited to, *Saccharomyces*/xylinum black tea ferment, *Anemarrhena asphodeloides* root extract, sodium hyaluronate, and the like. Exemplary hair growth retardation agents include, but are not limited to, ursolic acid, phytosphingosine, *Boswella serrata* extract, and the like. Exemplary hair growth stimulating agents include, but are not limited to, *Serenoa serrulata* fruit extract, licorice extract, acetyl glucosamine, and the like. Exemplary dark circle reduction or de-puffing agents include, but are not limited to, hesperidin methyl chalcone, dipeptide-2, *Passiflora incarnate* flower extract, linoleic acid, isolinoleic acid, and the like. Exemplary collagen synthesis or blood circulation enhancing agents include, but are not limited to, arginine, *Ascophyllum nodosum* extract, *Asparagopsis armata* extract, caffeine, and the like. Exemplary antioxidants include, but are not limited to, nordihydroguaiaretic acid, grape seed extract, green tea leaf extract, and the like.

The skin benefit agents as described hereinabove can be formulated into an ink formulation that is compatible with the printing device of the present invention. Such ink formulation may be an aqueous solution or an oil-in-water emulsion. When all the skin benefit agents to be delivered are water-soluble, it is preferred that the ink formulation is aqueous. When some of the skin benefit agents are oil-soluble, the ink formulation is preferably a micronized emulsion (suspension) containing an oil phase in form of micronized oil droplets dispersed in a continuous aqueous phase. Alternatively, non-water soluble skin benefit agents can be formulated in the solvent based ink formulation to overcome the solubility issue of the active with water based ink formulation.

Figure 1:
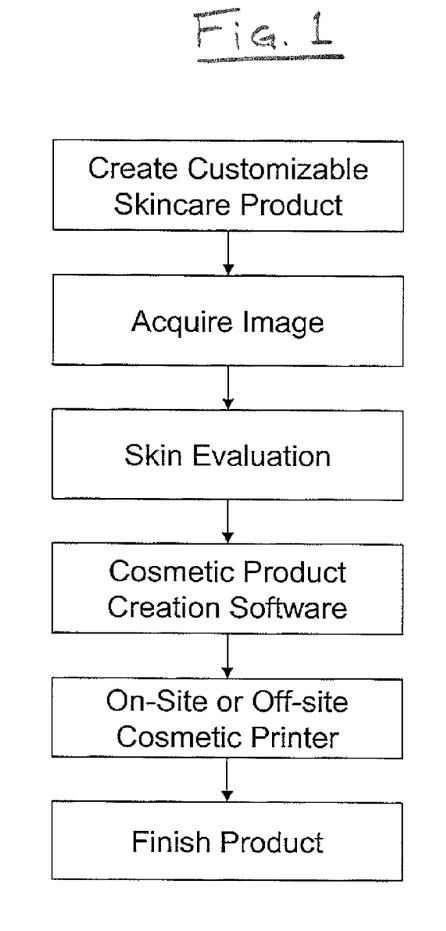
FIG. 1 is a flow diagram representing the overall systems and methods of the invention.

FIG. 1 is a flow diagram representing the overall concept systems and methods of the invention. The first box is the step of creating customizable skincare products, i.e., products that can be adjusted for individual users. The second step is to acquire an image of the user. The third step is skin evaluation. The fourth step involves the cosmetic product creation software. The fifth step involves the on-site or off-site cosmetic printer. And the last step is to finish the product. Each step is described in further detail in the following paragraphs.

Figure 2:
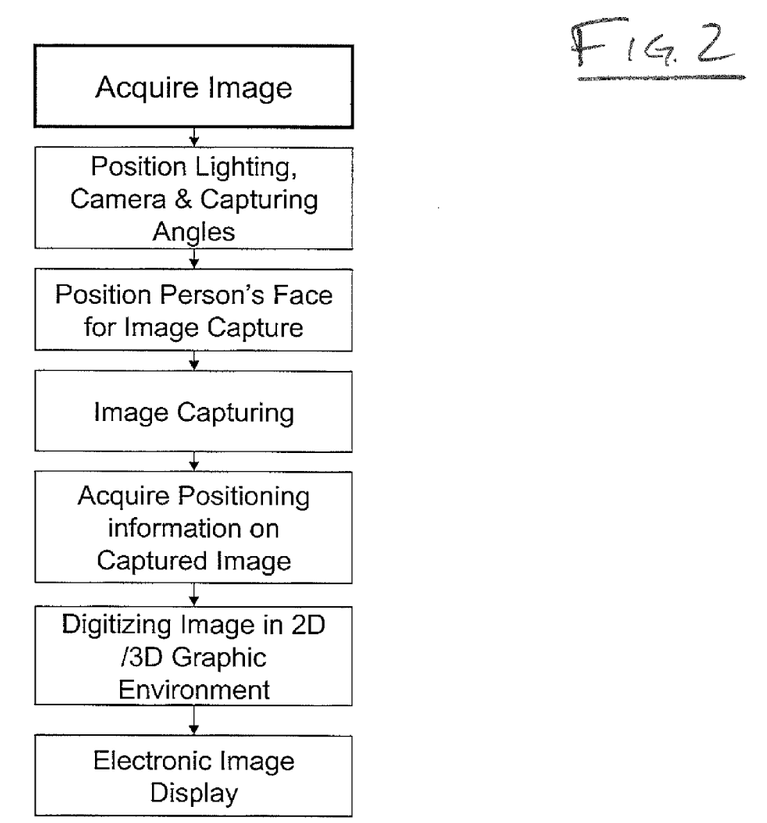
FIG. 2 is a flow diagram showing further details of the image acquisition step of the overall system shown in FIG. 1.

FIG. 2 is a flow diagram showing further details of the image acquisition step of the overall system shown in FIG. 1. First, lighting, camera(s) and other equipment is positioned to capture an image. Then the image is captured. The image may be captured with either a high end digital camera or video camera, or just a consumer grade camera, such as, for example, a cell phone or point-and-shoot camera. Preferably, more than one image of the user is captured, each from a different angle such that an analysis can be accomplished, for example, of the entire face. Along with the image(s), positioning information is acquired with respect to the captured image(s)—this may be accomplished on a pixel or other basis. The acquired or established positioning information on the image may be analyzed to determine surface topography, for mapping landmarks (e.g., the corners of the mouth or eyes), and eventually mapping the loci of the problem and/or treatment areas. The image is digitized in two-dimensional or three-dimensional graphic environment. Finally, the electronic image is displayed.

Figure 3:
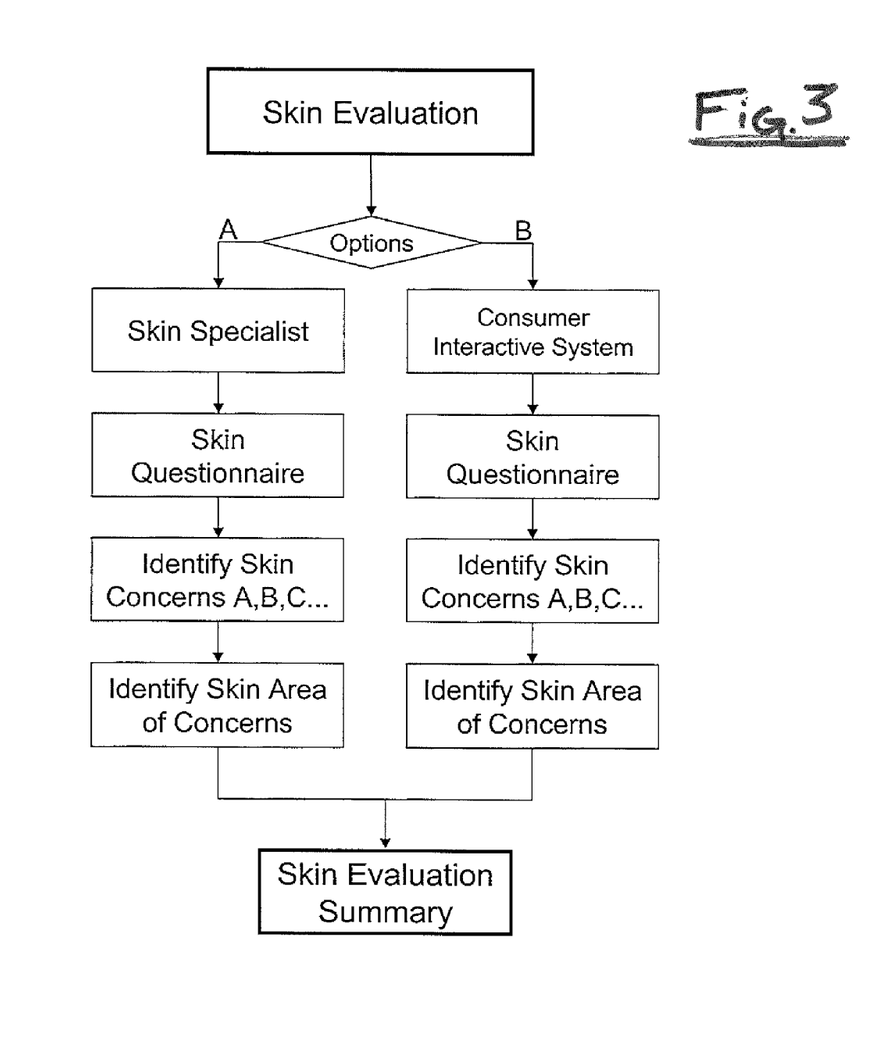
FIG. 3 is a flow diagram showing further details of one embodiment of the skin evaluation step of the overall system shown in FIG. 1.

FIG. 3 is a flow diagram showing further details of one embodiment of the skin evaluation step of the overall system shown in FIG. 1. Skin concerns addressed could be, for example, lines and wrinkles, age spots, dark circles, deep lines, sagging skin, etc. The skin evaluation may follow one of two paths. Optional path A involves evaluation by a skin specialist (also referred to herein as a beauty operator), such as, for example, a dermatologist, a beauty advisor, a cosmetician, a dermatologist or a sales associate associated with cosmetic product sales or recommendation in, for example, a beauty counter environment in a brick-and-mortar type retail store or online shopping venue. A skin questionnaire is used to guide the evaluation. The evaluation identifies particular skin concerns A, B, C, etc. and identifies the skin areas of the concerns. Path A results in a skin evaluation summary. Alternatively, path B involves a consumer interactive system. This also includes a skin questionnaire that guides the evaluation to identify skin concerns A, B, C, etc. and identify the skin areas of concerns. Path B similarly results in a skin evaluation summary.

Figure 4:
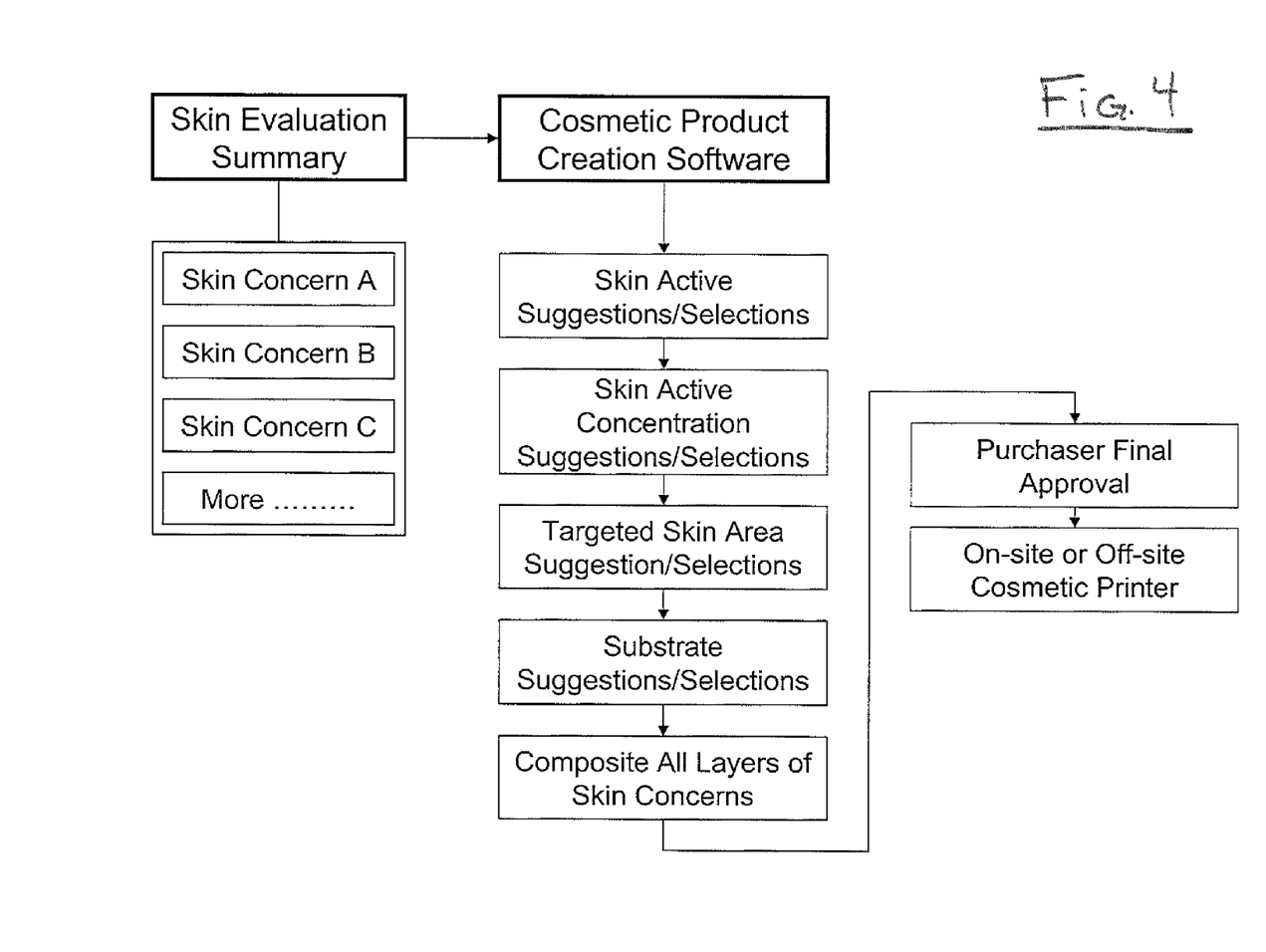
FIG. 4 is a flow diagram showing further details of the skin evaluation summary and the cosmetic product creation software step of the overall system shown in FIG. 1.

FIG. 4 is a flow diagram showing further details of the skin evaluation summary and the cosmetic product creation software step of the overall system shown in FIG. 1. The skin evaluation summary includes the skin concerns A, B, C, etc. The cosmetic product creation software receives the skin evaluation summary. The cosmetic product creation software is programmed to generate skin active suggestions and selections. It is further programmed to generate skin active concentration suggestions and recommendations. The cosmetic product creation software is programmed to generate suggestions and selections of cosmetics for a targeted skin area. The software is further programmed to generate substrate suggestions and selections. It creates a composite of all layers of skin concerns. It provides the user with the opportunity to give final approval for the suggestions and recommendations. Once approval is given, the suggestions and recommendations are sent to the cosmetic printer, either on-site or off-site, to create the custom treatment product.

Figure 5:
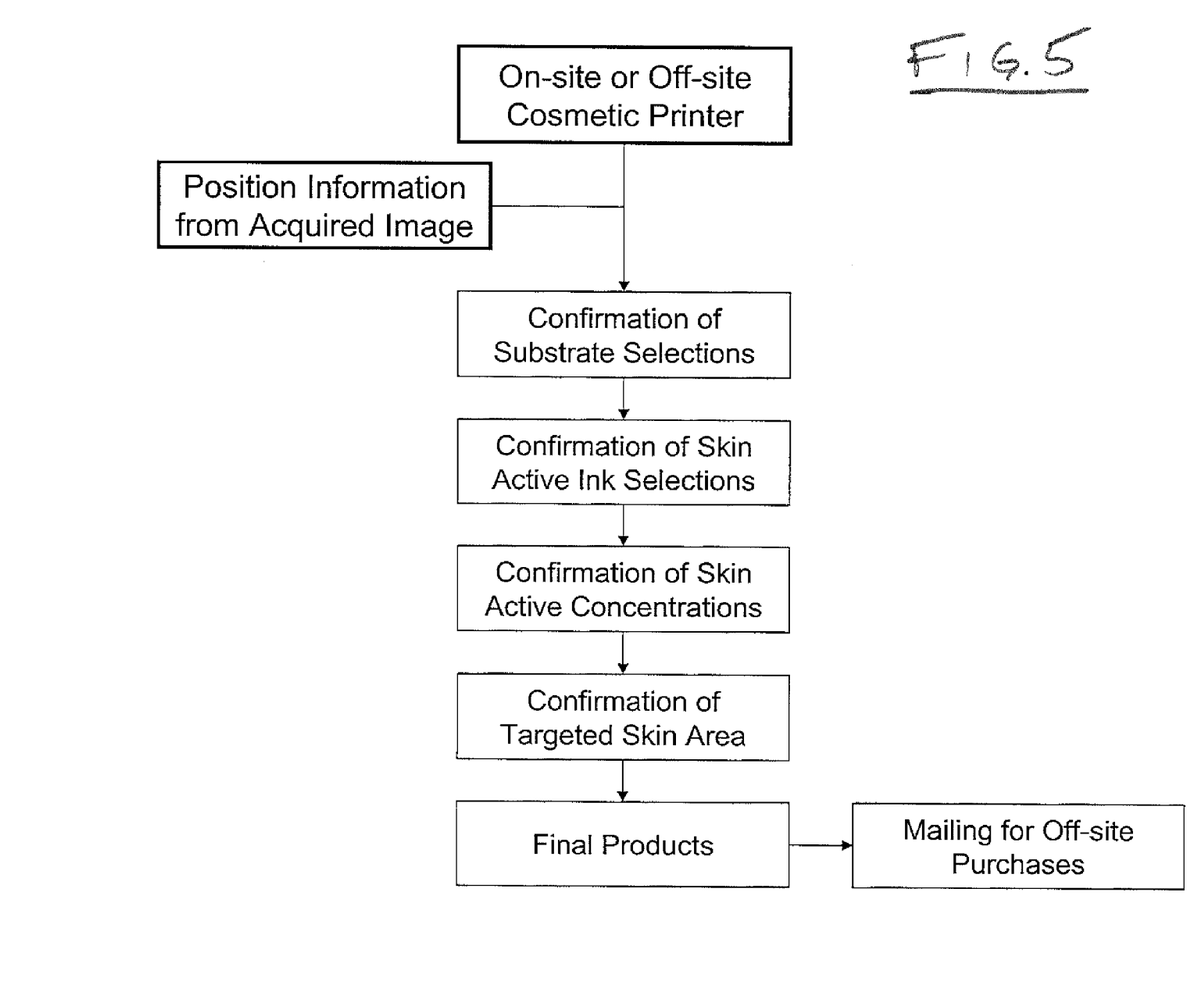
FIG. 5 is a flow diagram showing further details of the on-site or off-site printer step of the overall system shown in FIG. 1.

FIG. 5 is a flow diagram showing further details of the on-site or off-site printer step of the overall system shown in FIG. 1. The printer, either on-site or off-site, receives the suggestions and recommendations from the cosmetic product creation software. The printer also receives the position information from the acquired image of the user. Software associated with the printer confirms the substrate selections, the skin active ink selections, the skin active concentration levels and the targeted skin areas (locations). It then prints the final product. If the printer is on-site, the final product is provided directly to the user. If the printer is off-site, the final product is shipped to the user, or the user is encouraged to return to the point-of-sale (retail location) to pick up the printed mask—i.e., it encourages a second visit to the store. The final product is, for example, a full face mask as described in the following paragraphs.

Figure 6:
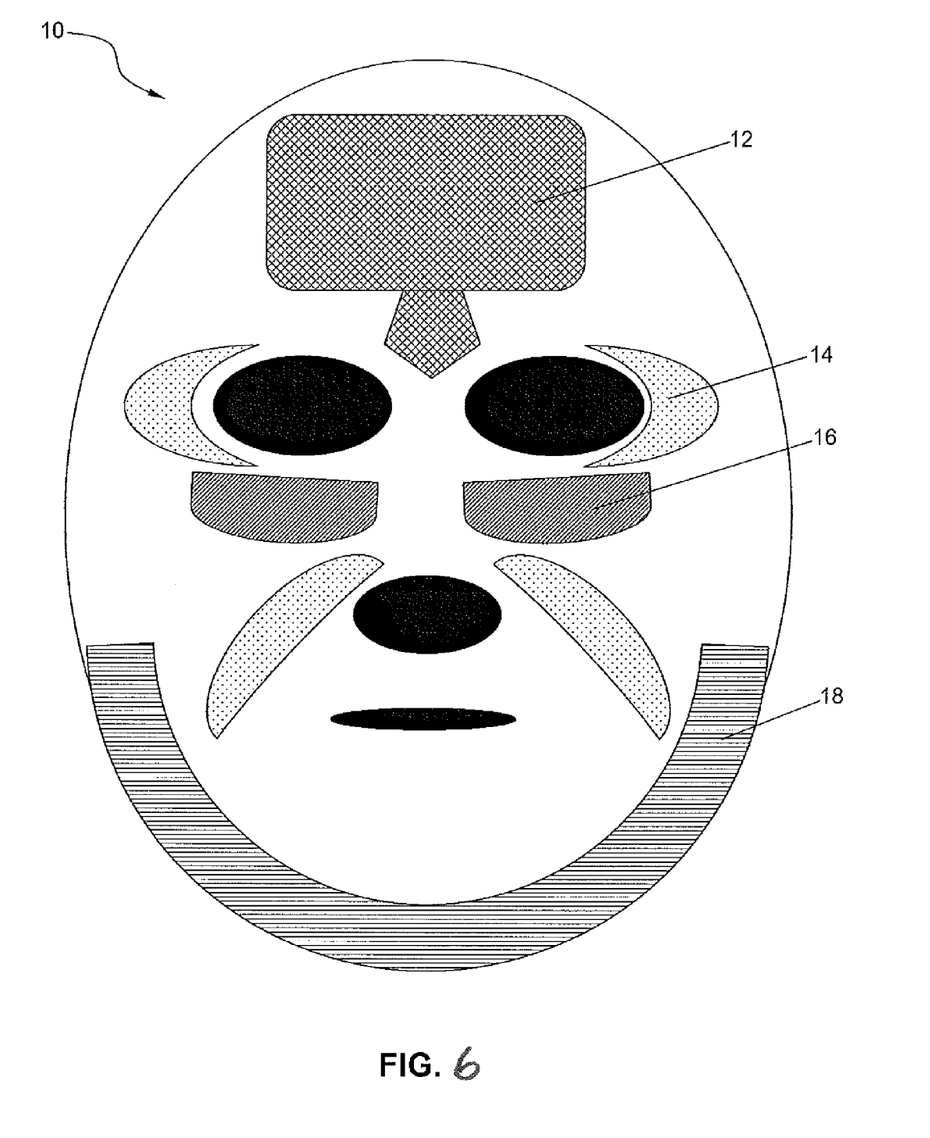
FIG. 6 is a schematic representation of a facial mask containing multiple isolate, discrete regions with different skin benefit agents, according to one embodiment of the present invention.

FIG. 6 is a schematic view of a facial mask 10 according to one embodiment of the present invention. The facial mask 10 contains multiple discrete regions 12, 14, 16, and 18, which are isolated from one another. Based on the particular skin conditions of the user, regions 12 are imprinted with at least one sebum controlling agent for reducing the oiliness at the T-zone section of the user's face; regions 14 are imprinted with at least one wrinkle reduction or skin-tightening agent for reducing the fine lines and wrinkles at the corners of the user's eyes and mouth; regions 16 are imprinted with at least one dark circle reduction or de-puffing agent; and region 18 is imprinted with at least one anti-cellulite agent. Of course, the discrete regions themselves, may also be customized based on a skin profiling analysis. Customizations include size, shape and number of discrete regions. Preferably, but not necessarily, different regions on the mask 10 may be marked with different colors for easy alignment with different facial features for which the skin benefit agents are intended. FIG. 2 is a schematic representation of a facial mask 10 according to a second embodiment of the present invention.

Figure 7:
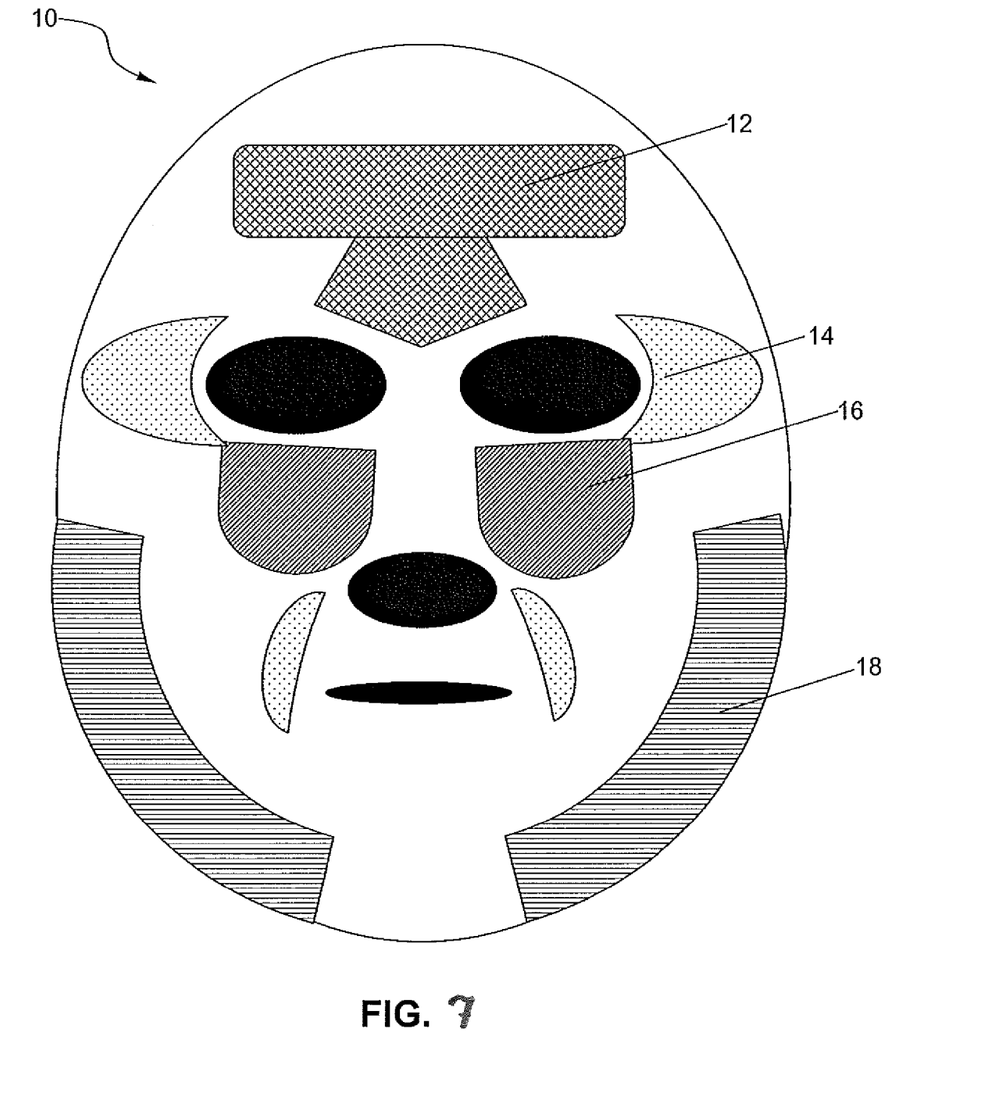
FIG. 7 is a schematic representation of a facial mask according to a second embodiment of the present invention.
Figure 8:
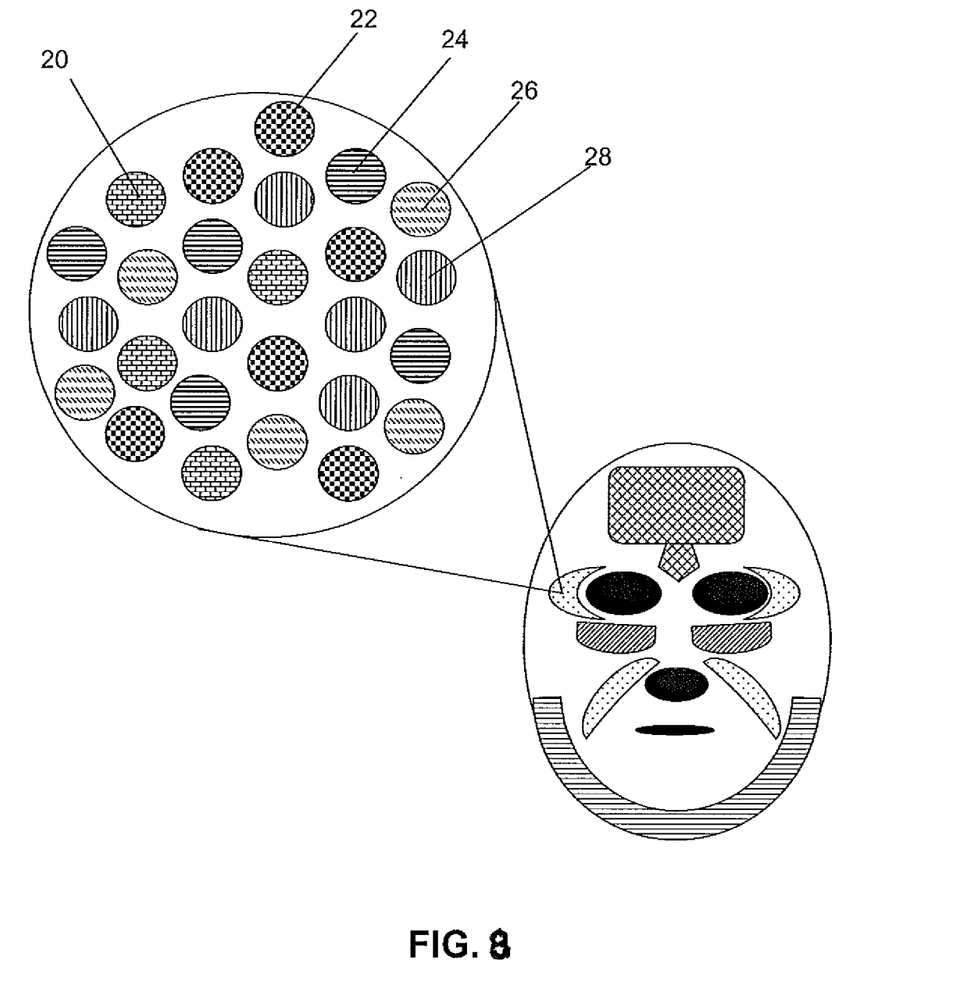
FIG. 8 is an exploded view of one isolate, discrete region on the facial mask of FIG. 1.

FIG. 7 shows an exploded view of the region 14 of FIG. 1. Five different types of skin benefit agents are printed thereon, which include a wrinkle reduction or skin-tightening agent 20, an anti-aging agent 22, an antioxidant agent 24, a moisturizing agent 26, and a plumping agent 28. These skin benefit agents are deposited onto the substrate as separate droplets, which are scattered among one another but without being mixed with one another. In this manner, such skin benefit agents can provide simultaneous treatment to the corners of the user's eyes and mouth with minimum or no interference with one another.

It will be understood by those skilled in the art that, while gel cosmetic sheets suitable for use in the present invention, are naturally tacky, a cosmetic sheet comprised of paper or a textile may require the presence of a cosmetically acceptable adhesive layer associated with the first surface of the support to enhance adherence to the skin. The adhesion of the sheet to the skin may occur via an adhesive compound associated with the surface of the sheet or it may be provided in the form of a gel or liquid, such as water, which moistens the sheet which then clings to skin. The user may also apply the mask to pre-moistened skin. It also is contemplated that a consumer could introduce a liquid activator to the sheet or to specific areas of the sheet which could serve to aid in adhesion of the sheet to the skin, to activate the impregnated formulation, or both. The cosmetic sheet may also be provided with a supporting sheet which can be removed, e.g. peeled away, before the sheet is applied to the skin.

The cosmetic sheet may be formed of any thin, porous, flexible absorbent material, including woven and non-woven fabrics, including felts, paper, natural fibers, synthetic fibers, elastic blends or a mixture thereof. Non-limiting examples include cotton, linen, rayon, thermoplastics, and cellulosics. The sheet material may be a water-soluble material, such as sugar or polysaccharides, collagen, and water-soluble film-forming polymers. The sheet material may also comprise a gel, such as a hydrogel, comprised of, for example, agarose or a water-soluble low-substituted cellulose ether which may include methyl cellulose, hydroxyethyl cellulose, hydroxypropyl cellulose, hydroxypropylmethyl cellulose, hydroxypropylhydroxyethyl cellulose, hydroxyethylmethyl cellulose, ethyl cellulose, hydroxyethylethyl cellulose, or carboxymethyl cellulose. Non-woven fabrics are especially preferred from the viewpoints of cost, productivity and aesthetic feel. Examples of preferred non-woven materials include, but are not limited to, natural and synthetic felts, rice paper or cloth, and bamboo cloth. In a preferred but not necessary embodiment of the present invention, both the substrate and the skin benefit agents of the cosmetic sheet are completely water-soluble, such as sugar or collagen, so upon application of water or like liquid activator, the cosmetic sheet softens and conforms to the skin, and subsequently, the entire sheet is absorbed by the skin surface without having to be removed. Commercially available cosmetic sheets suitable for practice of the present invention include, for example, the sugar-based Frosting Sheets from Kopykake (Torrance, Calif.), the Matricol® Collagen Sheets from Dr. Suwelack Skin & Health Care AG (Billerbeck, Germany), and the 3M™ Transparent 2.6 mil Polyethylene Medical Tape 9830.

Example 1

Targeted Delivery of Caffeine Power

An aqueous solution containing caffeine power was prepared by mixing the following ingredients together:

| Ingredients | wt % |
| --- | --- |
| Deionized water | QS |
| Butylene glycol | 15.00 |
| Caffeine | 5.00 |
| FD&C Blue No. 1 | 0.04 |
| Phenoxyethanol | 0.50 |
| Total | 100.00 |

The FD&C Blue No. 1 color was provided to mark regions with caffeine power printed thereon. The aqueous solution as described hereinabove was placed into a refillable ink cartridge of an Epson Workforce 30 inkjet printer, which was in turn connected to a personal computer installed with Photoshop Element 4.0. Three different types of substrate sheets, including a sugar-based Frosting Sheet from Kopykake (Torrance, Calif.), a Matricol® Collagen Sheet from Dr. Suwelack Skin & Health Care AG (Billerbeck, Germany), and a 3M™ Transparent 2.6 mil Polyethylene Medical Tape 9830 were fed to the paper tray of the Epson Workforce 30 inkjet printer, and the caffeine-containing aqueous solution was successfully printed onto the substrate sheets by the inkjet printer. The printed substrate sheets were then applied to the skin of a user for targeted delivery of caffeine as a skin benefit agent.

Example 2

Targeted Delivery of Salicylic Acid

An aqueous solution containing salicylic acid was prepared by mixing the following ingredients together:

| Ingredients | wt % |
| --- | --- |
| Deionized water | QS |
| Isopentyldiol | 40.00 |
| Salicylic acid | 1.00 |
| FD&C Yellow No. 5 | 0.04 |
| Phenoxyethanol | 0.50 |
| Total | 100.00 |

The FD&C Yellow No. 5 color was provided to mark regions with salicylic acid (SA) printed thereon. The aqueous solution as described hereinabove was placed into a refillable ink cartridge of an Epson Workforce 30 inkjet printer, which was in turn connected to a personal computer installed with Photoshop Element 4.0. Three different types of substrate sheets, including a sugar-based Frosting Sheet from Kopykake (Torrance, Calif.), a Matricol® Collagen Sheet from Dr. Suwelack Skin & Health Care AG (Billerbeck, Germany), and a 3M™ Transparent 2.6 mil Polyethylene Medical Tape 9830 were fed to the paper tray of the Epson Workforce 30 inkjet printer, and the SA-containing aqueous solution was successfully printed onto the substrate sheets by the inkjet printer. The printed substrate sheets were then applied to the skin of a user for targeted delivery of SA as a skin benefit agent.

Example 3

Targeted Delivery of Argireline Solution NP (Acetyl Hexapeptide-8)

An aqueous solution containing Argireline Solution NP was prepared by mixing the following ingredients together:

| Ingredients | wt % |
| --- | --- |
| Deionized water | QS |
| Argireline Solution NP | 62.50 |
| Purified Water: 99.35 wt % | |
| Acetyl Hexapeptide-8: 0.05 wt % | |
| Phenoxyethanol: 0.50 wt % | |
| Potassium Sorbate: 0.10 wt % | |
| 1,3 Butylene Glycol | 15.00 |
| PEG-11 Methyl Ether Dimethicone (KF-6011) | 0.10 |
| Caprylyl Glycol (Lexguard O) | 0.30 |
| Potassium Sorbate | 0.09 |
| FD&C Red No. 4 (1% Aq Soln W.B.G) | 0.20 |
| Citric Acid 10% Solution | 0.21 |
| Total | 100.00 |

The aqueous solution as described hereinabove was placed into a refillable ink cartridge of an Epson Workforce 30 inkjet printer, which was in turn connected to a personal computer installed with Photoshop Element 4.0. Three different types of substrate sheets, including a sugar-based Frosting Sheet from Kopykake (Torrance, Calif.), a Matricol® Collagen Sheet from Dr. Suwelack Skin & Health Care AG (Billerbeck, Germany), and a 3M™ Transparent 2.6 mil Polyethylene Medical Tape 9830 were fed to the paper tray of the Epson Workforce 30 inkjet printer, and the Argirelene-containing aqueous solution was successfully printed onto the substrate sheets by the inkjet printer. The printed substrate sheets were then applied to the skin of a user for targeted delivery of Argirelene (Acetyl Hexapeptide-8) as a skin benefit agent.

Note that color is optional in the foregoing examples.

Figure 9:
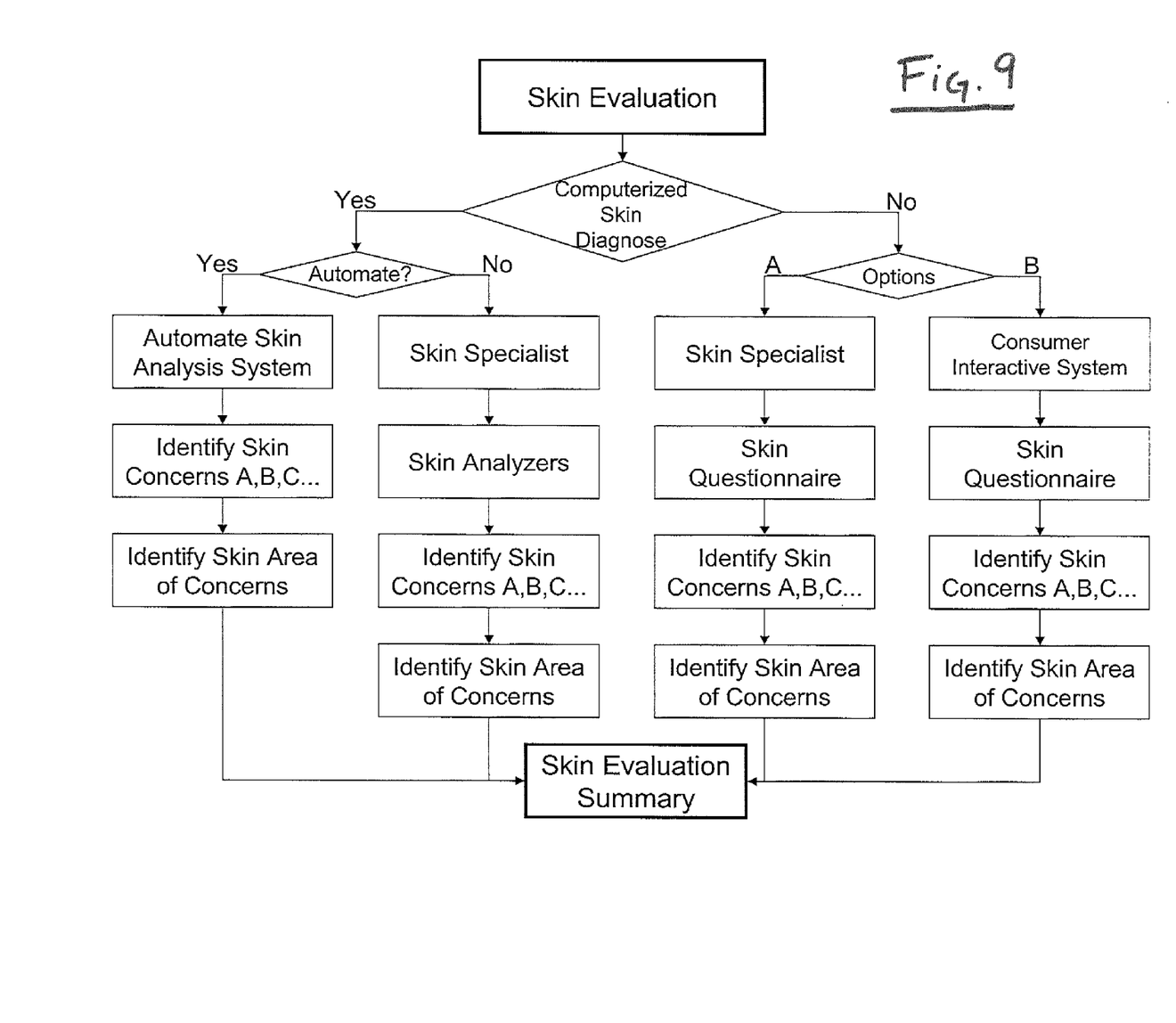
FIG. 9 is a flow diagram showing further details of alternative embodiments of the skin evaluation step of the overall system shown in FIG. 1.

FIG. 9 is a flow diagram showing further details of two alternative embodiments of the skin evaluation step of the overall system shown in FIG. 1 involving computerized skin diagnosis. The flow diagram shows 4 alternate paths from left to right: 1) Automated Skin Analysis System (fully automatic), 2) Skin Specialist using Skin Analyzers (semi-automatic), 3) Skin Specialist using Questionnaire, and 4) Consumer Interactive System using Questionnaire. Note that paths 3 and 4, the two paths on the right side of the flow diagram illustrated in FIG. 9 showing the 'manual' or non-automated skin diagnosis, are the same as the two paths shown in the flow diagram illustrated in FIG. 1 and previously described herein. The additional embodiments are paths 1 and 2 on the left side of the flow diagram illustrated in FIG. 9. Paths 1 and 2 on the left side in FIG. 9 show alternative paths for fully 'automated' or 'automatic' computerized skin diagnosis (path 1, the path furthest to the left) and semi-automated or semi-automatic computerized skin diagnosis (path 2, the path second from the left). The fully automated skin analysis path has a first step of providing an automate skin analysis system, e.g., a system that may include imaging and/or sensors and/or probes for gathering data. A second step involves automated identification of skin concerns A, B, C, etc. A third step involves identifying skin area of concerns. The path then results in a skin evaluation summary. In the semi-automatic path second from the left, a skin specialist is involved as well as skin analyzers (e.g., equipment such as imagers, sensors and probes) that are manipulated by the skin expert. The skin specialist manipulates the skin analyzers to identify the skin concerns A, B, C, etc. and identify the skin area of concerns. This path also results in a skin evaluation summary. No matter what path is utilized, automatic, semi-automatic, manual/skin specialist or manual/consumer interactive, the result is a skin evaluation summary that can be entered into the cosmetic product creation software to create the custom cosmetic product.

Although the present invention has been described in accordance with preferred embodiments, it will be understood by those skilled in the art that various changes and modifications may be made without departing from the spirit and scope of the invention.

What is claimed is:

1. A method for targeted and individualized delivery of multiple skin benefit agents to the skin of a user comprising:
    capturing an image of a predetermined treatment area of the user's skin;
    analyzing the captured image for mapping the predetermined treatment area;
    capturing selective data inputs from an input device;
    generating from the selective data inputs a skin profile indicative of the conditions of the predetermined treatment area of the user's skin;
    processing the captured image, the mapping and the skin profile to generate a virtual 3D image of the user's face or head showing the conditions of the predetermined treatment area; and
    generating a cosmetically active product based on the generated skin profile, wherein the product contains different skin benefit agents for treating the indicated conditions of the predetermined treatment area and wherein said product is a cosmetic delivery sheet arranged and constructed for conforming to the predetermined treatment area of the user's skin, and wherein said cosmetic delivery sheet comprises a substrate with multiple isolate, discrete regions, wherein at least two of the isolate, discrete regions are imprinted with different skin benefit agents for treating different skin conditions of the predetermined treatment area.

2. The method of claim 1 wherein the input device is at least one or a combination of a keyboard, a touch screen, a computer, a personal digital assistant, a cell phone, a smart phone, a point-of-sale terminal, a kiosk and a workstation.

* * * * *